(12) United States Patent
Ho

(10) Patent No.: US 12,350,457 B2
(45) Date of Patent: Jul. 8, 2025

(54) URETERAL STENT ASSEMBLY AND STENT PUSHER THEREOF

(71) Applicant: Chen-Hsun Ho, Taipei (TW)

(72) Inventor: Chen-Hsun Ho, Taipei (TW)

( * ) Notice: Subject to any disclaimer, the term of this patent is extended or adjusted under 35 U.S.C. 154(b) by 409 days.

(21) Appl. No.: 18/171,651

(22) Filed: Feb. 20, 2023

(65) Prior Publication Data

US 2023/0264002 A1 Aug. 24, 2023

(30) Foreign Application Priority Data

Feb. 23, 2022 (TW) .................................. 111106626

(51) Int. Cl.
*A61M 27/00* (2006.01)

(52) U.S. Cl.
CPC ... *A61M 27/008* (2013.01); *A61M 2210/1089* (2013.01)

(58) Field of Classification Search
CPC ........................... A61M 25/003; A61M 27/008
See application file for complete search history.

(56) References Cited

U.S. PATENT DOCUMENTS

| 10,070,978 | B2 | 9/2018 | Ponsky et al. |
| 10,500,073 | B2 | 12/2019 | Ponsky et al. |
| 2017/0319324 | A1 | 11/2017 | Ponsky et al. |

FOREIGN PATENT DOCUMENTS

| CN | 203447616 U | 2/2014 |
| EP | 0516189 A1 | 12/1992 |
| TW | M629477 U | 7/2022 |

*Primary Examiner* — Leslie R Deak
(74) *Attorney, Agent, or Firm* — CKC & Partners Co., LLC

(57) ABSTRACT

A ureteral stent assembly includes a ureteral stent, a bladder portion, and a stent pusher. The bladder portion is connected to the ureteral end of the ureteral stent with a tether. The stent pusher includes a bladder portion pusher. When the ureteral stent and the bladder portion are pushed into a predetermined position of the human body along a guidewire by the stent pusher, the guidewire passes through the ureteral stent, the bladder portion and the stent pusher, and the front end of the stent pusher is used to abut against the ureteral end of the ureteral stent. The bladder portion is sleeved on the front section of the stent pusher, and the bladder portion pusher is used to abut against the bladder portion.

8 Claims, 8 Drawing Sheets

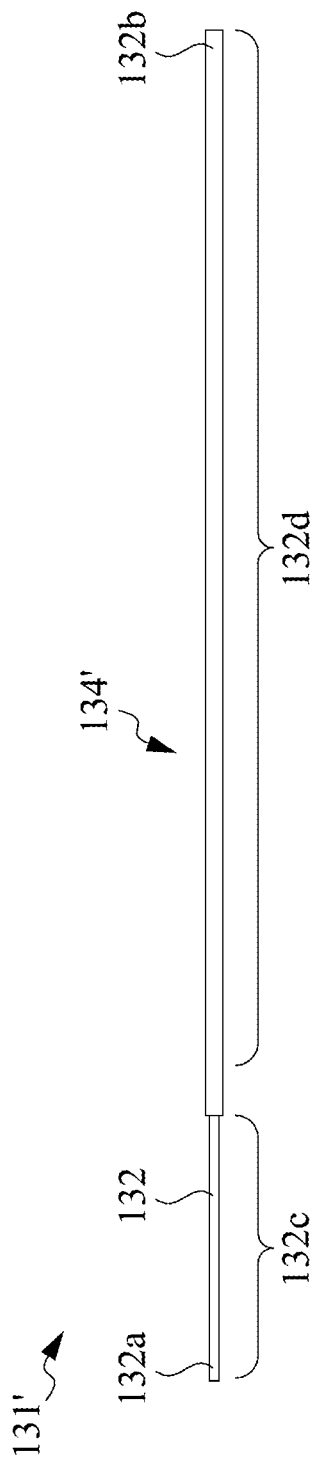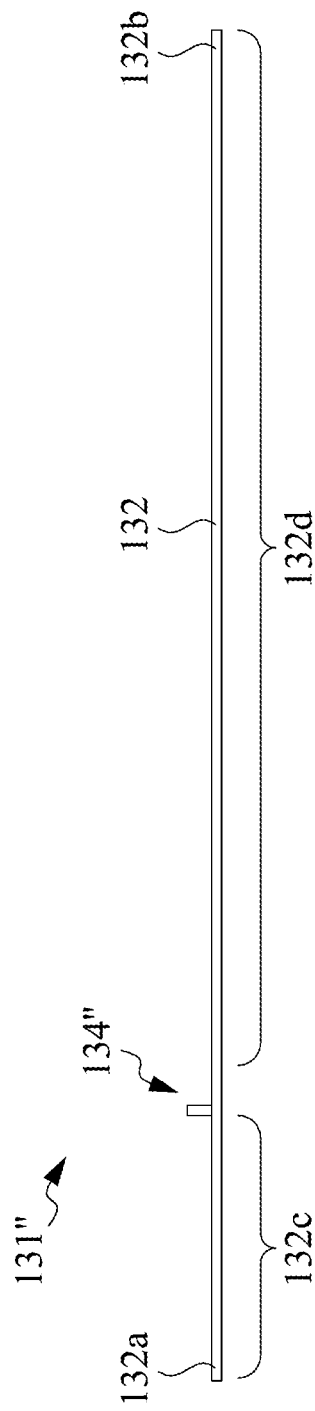

URETERAL STENT ASSEMBLY AND STENT PUSHER THEREOF

CROSS-REFERENCE TO RELATED APPLICATION

This application claims priority to Taiwan Application Serial Number 111106626, filed Feb. 23, 2022, which is herein incorporated by reference in its entirety.

BACKGROUND

Field of Disclosure

The present disclosure relates to a ureteral stent and an associated stent pusher.

Description of Related Art

A traditional ureteral stent is a device installed in the human body to assist urine drainage. By placing the two ends of the ureteral stent in the renal pelvis and bladder respectively, the obstruction of the ureter is prevented or treated to assure that the urine of the kidney can flow to the bladder to achieve the medical treatment effect.

US patent (U.S. Pat. No. 10,500,073 B2) discloses a ureteral stent including a bladder portion, a kidney portion, and one or more tethers coupling the bladder portion to the kidney portion. However, U.S. Pat. No. 10,500,073 B2 does not disclose a stent pusher to send such ureteral stent to desired positions in the human body.

US patent (U.S. Pat. No. 10,070,978 B2) discloses a stent pusher assembly. However, the stent pusher assembly is unable to send a conventional ureteral stent and its bladder portion to desired positions in the human body synchronously.

In view of this, manufacturers of related medical equipments or medical practitioners are eager to improve the design of the traditional ureteral stents to benefit the patient.

SUMMARY

The present disclosure provides a ureteral stent assembly and a stent pusher to deal with the needs of the prior art problems.

In one or more embodiments, a stent pusher is configured to advance a ureteral stent and a bladder portion that is connected to the ureteral stent by a tether. The stent pusher includes a push rod and a bladder portion pusher. The push rod has a front end configured to abut and advance a renal end of the ureteral stent and a front section configured to be sleeved by the bladder portion. The bladder portion pusher is located on the push rod and has a size or shape configured to advance the bladder portion.

In one or more embodiments, the bladder portion pusher is fixedly positioned on the push rod.

In one or more embodiments, the bladder portion pusher is slidably positioned on the push rod.

In one or more embodiments, the bladder portion pusher is detachably positioned on the push rod.

In one or more embodiments, the bladder portion pusher is positioned on a middle section of the push rod.

In one or more embodiments, the bladder portion pusher occupies a remaining section of the push rod except the front section of the push rod.

In one or more embodiments, the front section of the push rod includes the front end of the push rod.

In one or more embodiments, a ureteral stent assembly includes a ureteral stent, a bladder portion and a stent pusher. The ureteral stent has a renal end and a ureteral end. The bladder portion is connected to the ureteral end by a tether. The stent pusher includes a push rod and a bladder portion pusher on the push rod. When the ureteral stent and the bladder portion are pushed into a predetermined position of a human body along a guidewire by the stent pusher, the guidewire passes through the ureteral stent, the bladder portion and the push rod, and a front end of the push rod is configured to abut against the ureteral end of the ureteral stent, a front section of the push rod is configured to be sleeved by the bladder portion, and the bladder portion pusher is configured to abut against the bladder portion.

In one or more embodiments, the bladder portion is made from materials that are suspendable in urine.

In one or more embodiments, the bladder portion serves as a gripping end for removing the ureteral stent.

In one or more embodiments, the bladder portion pusher is positioned on a middle section of the push rod.

In one or more embodiments, the bladder portion pusher occupies a remaining section of the push rod except the front section of the push rod.

In one or more embodiments, the bladder portion has a straight line shape.

In one or more embodiments, the bladder portion has a curly shape.

In one or more embodiments, the bladder portion pusher is fixedly, slidably or detachably positioned on the push rod.

In sum, the ureteral stent assembly of the present disclosure includes a ureteral stent and a bladder portion, a length of the ureteral stent is less than a length of the human ureter. When a renal end of the ureteral stent is positioned in the human kidney, a ureteral end of the ureteral stent is still located in the human ureter. Therefore, the ureteral stent will not be a source of irritation to the bladder. A material density of the bladder portion and tether is less than that of water, so it can be suspended in the urine of the human bladder and less likely to irritate the bladder. The push rod is designed to push the ureteral stent and bladder portion, and push the ureteral stent and the bladder portion to a predetermined position in the human body synchronously and accurately.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows:

FIG. 7 illustrates a stent pusher according to another embodiment of the present disclosure;

FIG. 8 illustrates a stent pusher according to still another embodiment of the present disclosure.

DETAILED DESCRIPTION

Figure 1:
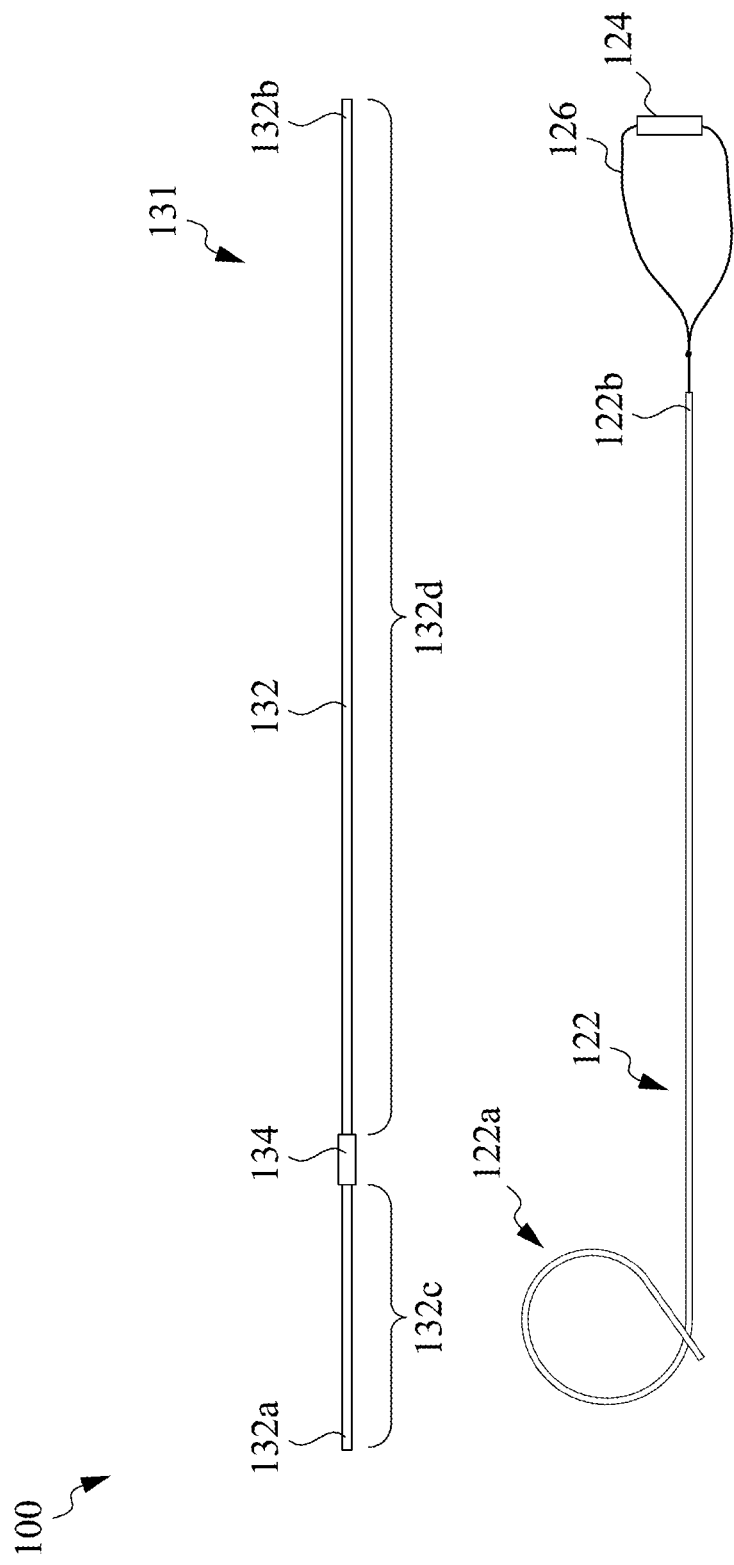
FIG. 1 illustrates a ureteral stent assembly according to some embodiments of the present disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1, which illustrates a ureteral stent assembly according to some embodiments of the present disclosure. A ureteral stent assembly 100 includes a ureteral stent 122, a bladder portion 124 and a stent pusher 131. The ureteral stent 122 includes a renal end 122a and a ureteral end 122b. The renal end 122a of the ureteral stent 122 is used to be placed in a human kidney, and the ureteral end 122b of the ureteral stent 122 is used to be placed in a human ureter, which is different from a conventional ureteral stent's usage. The bladder portion 124 is used to be placed in a human bladder, and is connected to the ureteral end 122b of the ureteral stent 122 with a tether 126. The stent pusher is a tool for pushing the ureteral stent 122 and bladder portion 124 into a predetermined position of a human body. The stent pusher 131 has a push rod 132 with a front end 132a and a rear end 132b. The front end 132a of the push rod 132 is used to abut against the ureteral stent 122, and the rear end 132b of the push rod 132 is hold by an operator for pushing the ureteral stent 122. The stent pusher 131 also includes a bladder portion pusher 134 located near the front end 132a of the push rod 132. The push rod 132 is divided into a front section 132c and a rear section 132d with the bladder portion pusher 134 as the segmentation point. In some embodiments of the present disclosure, the bladder portion pusher 134 can be positioned on the push rod 132 in a fixed, slidable or detachable manner. In some embodiments of the present disclosure, the renal end 122a of the ureteral stent 122 has a curly shape so that it can be positioned in the kidney of the human body. The renal end 122a of the ureteral stent 122 has appropriate elasticity, and when a relatively rigid guide wire passes through it, the renal end 122a will be in a straight line so as to facilitate delivery into the kidney of the human body during surgery. In some embodiments of the present disclosure, the bladder portion 124 is larger than an inner diameter of the human ureter. In some embodiments of the present disclosure, a material density of the bladder portion 124 is less than 1 gram per cubic centimeter, and is made of a material that does not irritate the human bladder. In some embodiments of the present disclosure, a material density of the tether 126 connected between the bladder portion 124 and the ureteral stent 122 may also be less than 1 gram per cubic centimeter. In some embodiments of the present disclosure, the bladder portion 124 has a straight line shape or a straight tube shape.

Figure 2:
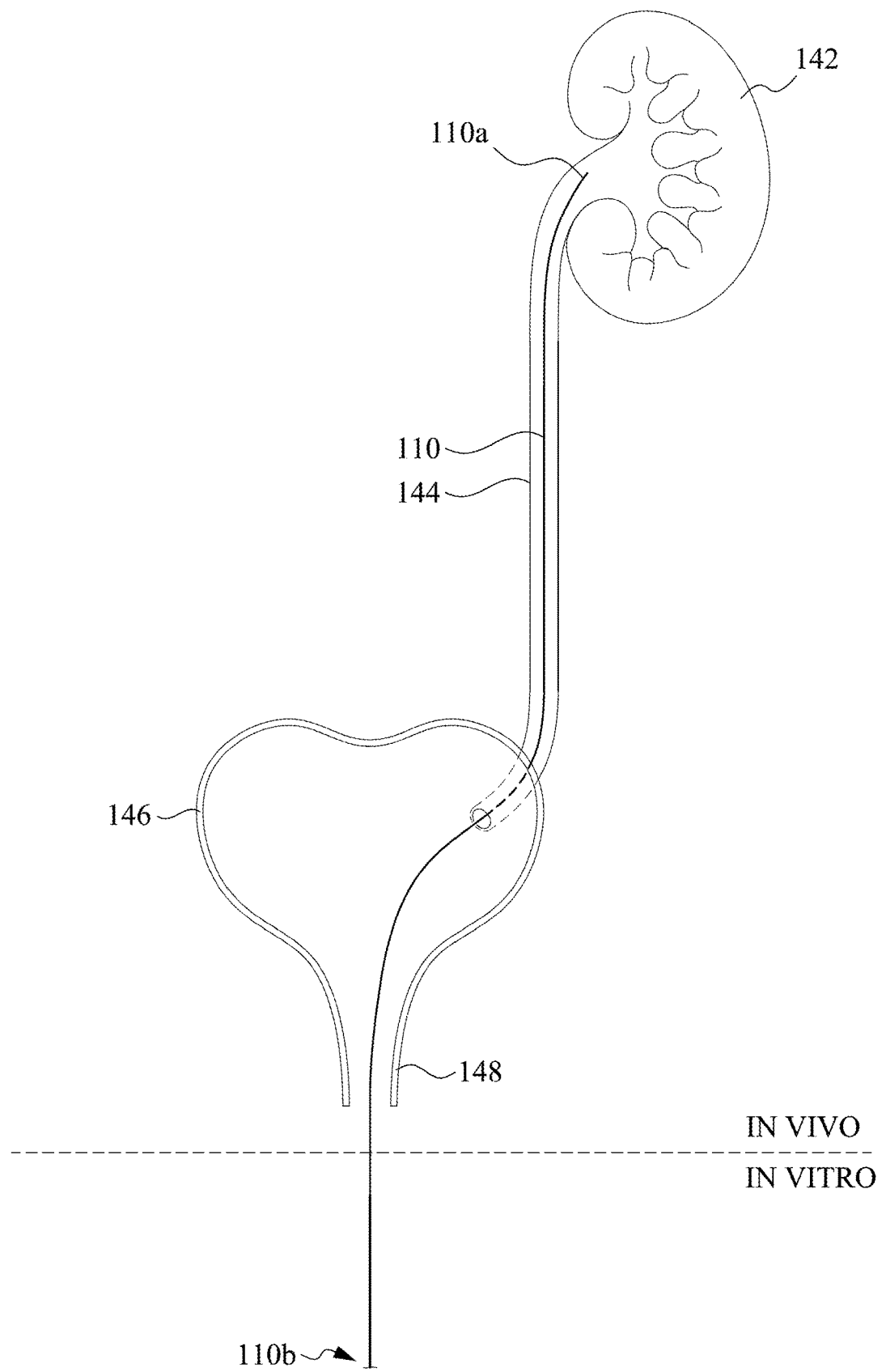
FIGS. 2-5 illustrate steps of moving a ureteral stent assembly into a human body according to some embodiments of the present disclosure.

Reference is made to FIGS. 2-5, which illustrate steps of moving a ureteral stent assembly into a human body according to some embodiments of the present disclosure. In the step of FIG. 2, it illustrates a schematic diagram of a human body part. Before placing the ureteral stent assembly into the human body, a guide wire 110 with appropriate rigidity and elasticity is placed into the human body, and a front end 110a of the guide wire 110 is placed in the kidney 142 along the urethra 148, bladder 146 and ureter 144. A rear end 110b of the guide wire 110 is placed outside the human body as a penetrating end of the ureteral stent assembly, so that the ureteral stent assembly can be transferred along the guide wire 110 into the predetermined position of the human body.

Figure 3:
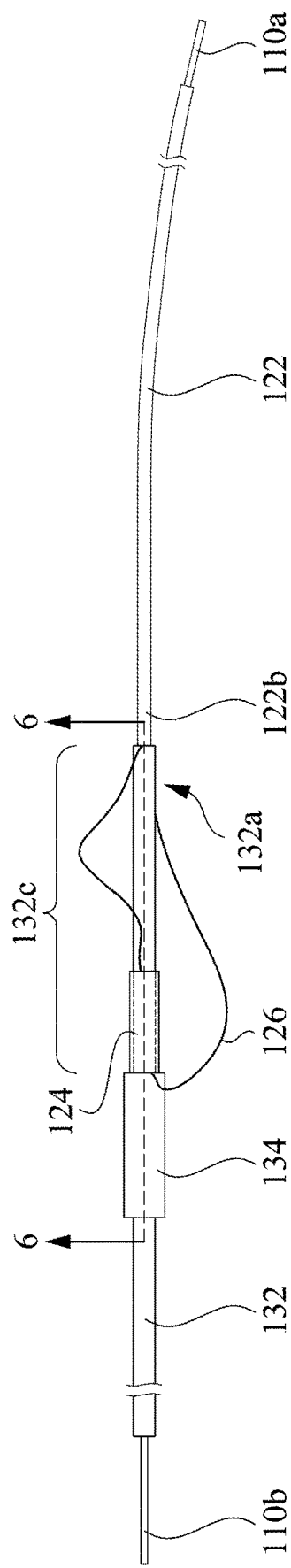

In the step of FIG. 3 (also referring to FIG. 1), the rear end 110b of the guide wire 110 is penetrated through the ureteral stent 122 (e.g., a hollow tube). The guide wire 110 is inserted from the renal end 122a of the ureteral stent 122 and out from the ureteral end 122b of the ureteral stent 122. The bladder portion 124 is then sleeved from the front end 132a of the push rod 132 onto its front section 132c, and the rear end 110b of the guide wire 110 is inserted into the push rod 132 (e.g., a hollow tube). The guide wire 110 is inserted from the front end 132a of the push rod 132 and pulled out from the rear end 132b of the push rod 132. The operator applies a force to the rear end 132b of the push rod 132, so that the front end 132a of the push rod 132 abuts against the ureteral end 122b of the ureteral stent 122, and advances the ureteral stent 122 into the human body along the guide wire 110. In some embodiments of the present disclosure, a length of the front section 132c of the push rod 132 should be at least greater than a length of the bladder portion 124, so that the bladder portion 124 can be sleeved on the front section 132c and be spaced from the ureteral end 122b of the ureteral stent 122 with a proper distance while being pushed into the human body.

Figure 4:
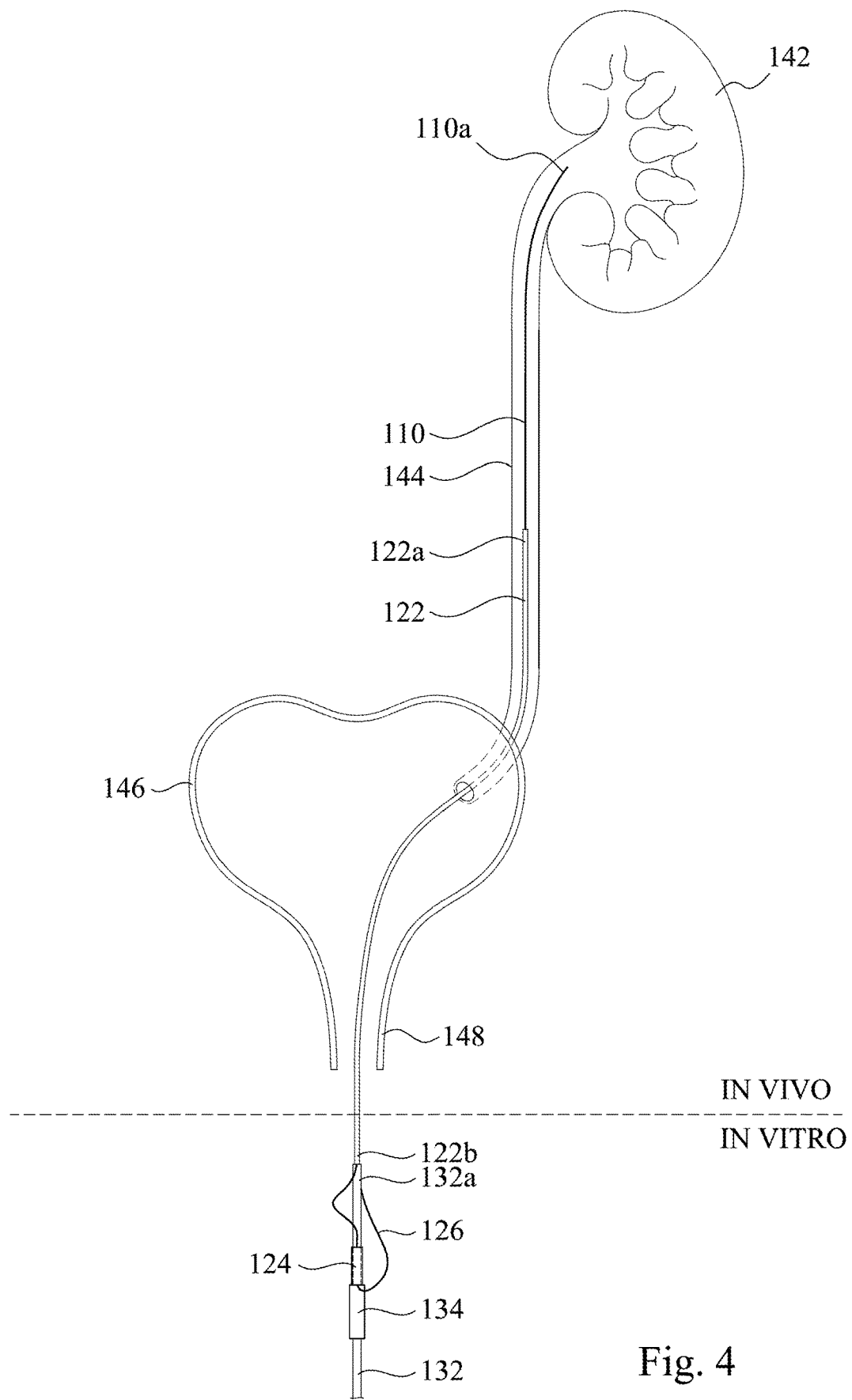

In the step of FIG. 4, under the pushing force of the push rod 132 by the operator, the ureteral stent 122 passes through the urethra 148 and the bladder 146 along the guide wire 110 and arrives at the ureter 144, and the bladder portion 124 also advances towards the bladder 146 simultaneously.

Figure 5:
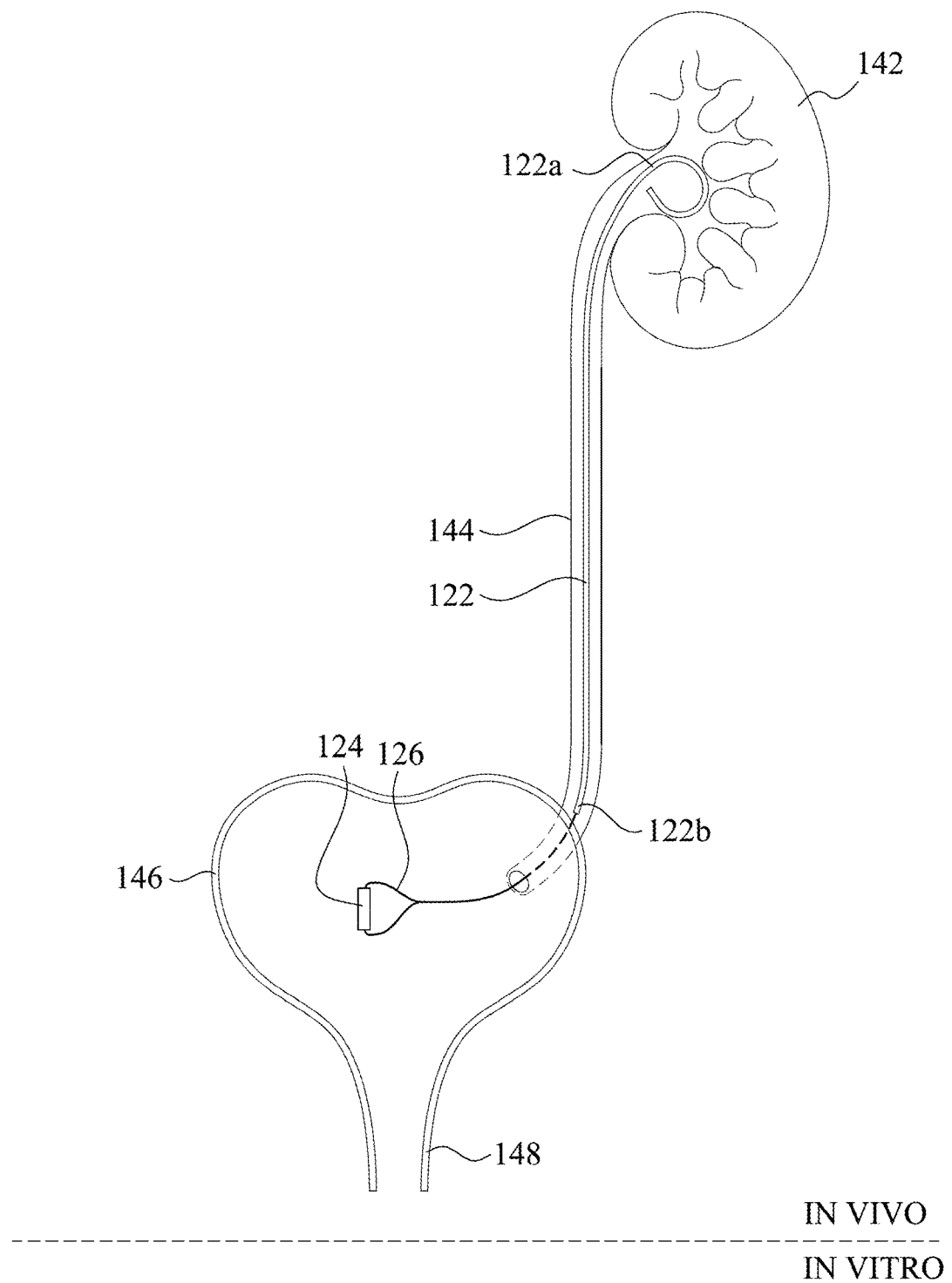

In the step of FIG. 5, under the pushing force of the operator, the renal end 122a of the ureteral stent 122 arrives at a predetermined position in the kidney 142, the ureteral end 122b of the ureteral stent 122 arrives at a predetermined position in the ureter 144, and the bladder portion 124 also reaches a predetermined position in the bladder 146. That is, under the push of the push rod 132, the ureteral stent 122 and the bladder portion 124 can reach the predetermined position in the human body synchronously. After the guide wire 110 is removed, the renal end 122a of the ureteral stent 122 recovers from the straight line to an original curly shape, and the size of the curled shape is larger than an inner diameter of the ureter 144, so that the renal end 122a can be positioned in the kidney 142 without entering the ureter 144. Since the bladder portion 124 is larger than the inner diameter of the ureter 144, the bladder portion 124 will not be entered into the ureter 144 during the pushing process. Because the material density of the bladder portion 124 and tether 126 is less than that of water (i.e., 1 gram per cubic centimeter), the bladder portion 124 and tether 126 will be suspended in the urine in the bladder 146 when the bladder 146 accumulates urine. Therefore, it is less likely to directly stimulate an inner wall of the bladder 146 so as to avoid discomfort or frequent urination issues. When a medical assistance task of the ureteral stent 122 is terminated and the ureteral stent 122 should be removed, a force can be applied to the bladder portion 124 during the operation to pull the ureteral stent 122 out of the kidney 142 and ureter 144 and out of the body. The ureteral stent 122 has no bladder end design and will not irritate the inner wall of the bladder, and the tether 126 is connected to the bladder portion 124, and the bladder portion 124 is used as a gripping end for removing the ureteral stent 122.

Figure 6:
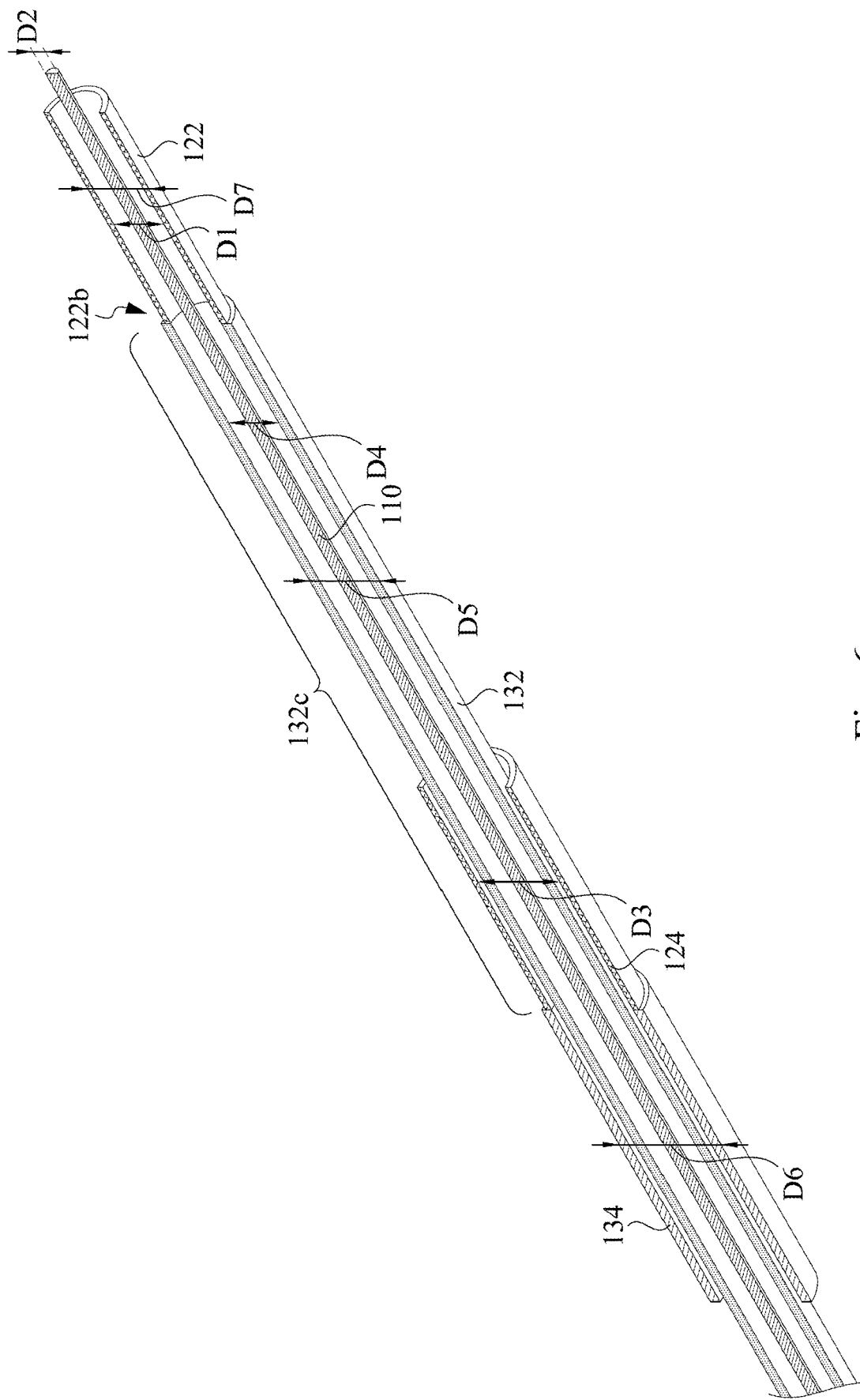
FIG. 6 illustrates a cross section view taken along cross sectional line 6-6 in FIG. 3.

Reference is made to FIG. 6, which illustrates a cross section view taken along the cross sectional line 6-6 in FIG. 3. In some embodiments of the present disclosure, an inner diameter D1 of the ureteral stent 122 is greater than an outer diameter D2 (about 0.88 mm) of the guide wire 110 such that the guide wire 110 can pass through the ureteral stent 122. In some embodiments of the present disclosure, an inner diameter D4 of the push rod 132 is greater than an outer diameter D2 of the guide wire 110 such that the guide wire 110 can pass through the push rod 132. In some embodiments of the present disclosure, an outer diameter D5 of the front section 132c of the push rod 132 should be greater than an inner diameter D1 of the ureteral stent 122, and the inner diameter D4 of the front section 132c of the push rod 132 should be smaller than an outer diameter D7 of the ureteral stent 122 such that the push rod 132 is able to advance the ureteral stent 122. In some embodiments of the present disclosure, an inner diameter D3 of the bladder portion 124 is greater than an outer diameter D5 of the front section 132c of the push rod 132 such that the bladder portion 124 can be sleeved on and slid along the front section 132c of the push rod 132. In some embodiments of the present disclosure, an outer diameter D6 of the bladder portion pusher 134 is greater than the inner diameter D3 of the bladder portion 124 such that the bladder portion pusher 134 can advance the bladder portion 124 to slide along the guide wire 110.

Reference is made to FIG. 7, which illustrates a stent pusher according to another embodiment of the present disclosure. In some embodiments of the present disclosure, the stent pusher 131' differs from the aforementioned stent pusher 131 mainly in the size or area covered by the bladder portion pusher 134'. Unlike the bladder portion pusher 134 which is only located in a middle section of the push rod 132, the bladder portion pusher 134' extends to cover the entire rear section 132d of the push rod 132. In other words, the bladder portion pusher 134' covers or occupies the rest or remaining section of the push rod 132 except the front section 132c.

Reference is made to FIG. 8, which illustrates a stent pusher according to still another embodiment of the present disclosure. In some embodiments of the present disclosure, the stent pusher 131" is different from the aforementioned stent pusher 131 mainly in its bladder portion pusher 134". In some embodiments of the present disclosure, the bladder portion pusher 134" can be any shape different from the bladder portion pusher 134 or the bladder portion pusher 134', for example, the size or shape of the bladder portion pusher 134" needs to be able to advance the above-mentioned bladder portion 124, does not require a special shape.

Figure 9:
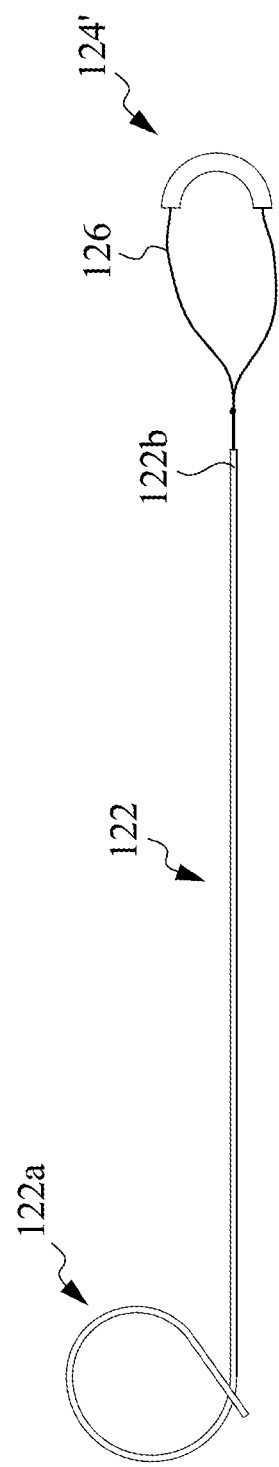
FIG. 9 illustrates a ureteral stent according to another embodiment of the present disclosure.

Reference is made to FIG. 9, which illustrates a ureteral stent according to another embodiment of the present disclosure. Unlike the straight line shape or straight tube shape of the aforementioned bladder portion 124, the bladder portion 124' of this embodiment has a curly shape or a curly tube shape, so that it can be positioned in the bladder of the human body, and is not easy to enter the ureter of the human body. Similar to the aforementioned characteristics of the renal end 122a of the ureteral stent 122, the bladder portion 124' has proper elasticity, and when the relatively rigid guide wire passes through it, the bladder portion 124' will be in a straight line to facilitate insertion into the bladder of the human body during surgery. When the guide wire is removed, the bladder portion 124' will return to a curly shape, which is not easy to enter the ureter of the human body. The curly shape of the bladder portion 124' is also easy for the operator to grasp during the operation, and the ureteral stent 122 is also removed from the kidney 142 and the ureter 144 along with the bladder portion 124'.

In sum, the ureteral stent assembly of the present disclosure includes a ureteral stent and a bladder portion, a length of the ureteral stent is less than a length of the human ureter. When a renal end of the ureteral stent is positioned in the human kidney, a ureteral end of the ureteral stent is still located in the human ureter. Therefore, the ureteral stent will not be a source of irritation to the bladder. A material density of the bladder portion and tether is less than that of water, so it can be suspended in the urine of the human bladder and less likely to irritate the bladder. The push rod is designed to abut the ureteral stent and bladder portion, and advance the ureteral stent and the bladder portion to a predetermined position in the human body synchronously and accurately.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A ureteral stent assembly comprising:
a ureteral stent having a renal end and a ureteral end;
a bladder portion connected to the ureteral end by a tether; and
a stent pusher comprising a push rod and a bladder portion pusher on the push rod, wherein
when the ureteral stent and the bladder portion are pushed into a predetermined position of a human body along a guidewire by the stent pusher, the guidewire passes through the ureteral stent, the bladder portion and the push rod, and a front end of the push rod is configured to abut against the ureteral end of the ureteral stent, a front section of the push rod is configured to be sleeved by the bladder portion, and the bladder portion pusher is configured to abut against the bladder portion; thereby enabling synchronous placement of both the stent and the bladder portion.

2. The ureteral stent assembly of claim 1, wherein the bladder portion comprises materials that are suspendable in urine.

3. The ureteral stent assembly of claim 1, wherein the bladder portion serves as a gripping end for removing the ureteral stent.

4. The ureteral stent assembly of claim 1, wherein the bladder portion pusher is positioned on a middle section of the push rod.

5. The ureteral stent assembly of claim 1, wherein the bladder portion pusher occupies a remaining section of the push rod except the front section of the push rod.

6. The ureteral stent assembly of claim 1, wherein the bladder portion has a straight line shape.

7. The ureteral stent assembly of claim 1, wherein the bladder portion has a curly shape.

8. The ureteral stent assembly of claim 1, wherein the bladder portion pusher is fixedly, slidably or detachably positioned on the push rod.

* * * * *